US009520050B2

(12) United States Patent
Ros

(10) Patent No.: US 9,520,050 B2
(45) Date of Patent: Dec. 13, 2016

(54) INTERCHANGEABLE PERSONAL SECURITY DEVICE WITH A COMMUNICATION ACCESSORY

(71) Applicant: Revolar, Inc., Denver, CO (US)

(72) Inventor: Jacqueline V Ros, Denver, CO (US)

(73) Assignee: REVOLAR, INC., Denver, CO (US)

( * ) Notice: Subject to any disclaimer, the term of this patent is extended or adjusted under 35 U.S.C. 154(b) by 0 days.

(21) Appl. No.: 14/581,951

(22) Filed: Dec. 23, 2014

(65) Prior Publication Data

US 2015/0109123 A1    Apr. 23, 2015

Related U.S. Application Data

(63) Continuation-in-part of application No. 14/197,058, filed on Mar. 4, 2014.

(60) Provisional application No. 61/851,225, filed on Mar. 4, 2013, provisional application No. 61/827,725, filed on May 27, 2013, provisional application No. 61/844,138, filed on Jul. 9, 2013.

(51) Int. Cl.
| | |
|---|---|
| *G08B 25/01* | (2006.01) |
| *G08B 15/00* | (2006.01) |
| *G08B 21/02* | (2006.01) |
| *A61B 5/00* | (2006.01) |

(52) U.S. Cl.
CPC ........... *G08B 25/016* (2013.01); *G08B 15/004* (2013.01); *G08B 21/0288* (2013.01); *A61B 5/681* (2013.01); *A61B 5/6822* (2013.01)

(58) Field of Classification Search
CPC . G08B 15/004; G08B 21/0288; G08B 25/016; A61B 5/6822; A61B 5/681
See application file for complete search history.

(56) References Cited

U.S. PATENT DOCUMENTS

| | | | |
|---|---|---|---|
| 5,228,449 A | 7/1993 | Christ et al. | |
| 6,561,978 B1 * | 5/2003 | Conn | A61B 5/0031 |
| | | | 600/309 |

(Continued)

OTHER PUBLICATIONS

U.S. Appl. No. 14/581,951, "Interchangeable Personal Security Device With a Communication Accessory," Office Action dated Jul. 1, 2015.

(Continued)

*Primary Examiner* — Hongmin Fan
(74) *Attorney, Agent, or Firm* — Kunzler Law Group

(57) ABSTRACT

An apparatus for personal security is disclosed that includes a portable accessory formed to receive an alerting device. The alerting device fits within a compartment of the portable accessory, and the portable accessory includes a communication device. The apparatus includes an alerting device with an alerting element. The alerting device is interchangeable with a plurality of portable accessories. One or more activation elements are disposed on the portable accessory and formed to activate the alerting device wherein the alerting element sends an alert signal to the communication device in response to receiving an activation signal from the one or more activation elements. In one embodiment, the alerting device sends the alert signal to the communication device in response to receiving the activation signal. In another embodiment, the communication device notifies one or more predefined contacts that an alert signal was sent in response to receiving the alert signal.

19 Claims, 8 Drawing Sheets

(56) References Cited

U.S. PATENT DOCUMENTS

| | | | |
|---|---|---|---|
| 8,249,547 B1 | 8/2012 | Fellner | |
| 8,466,795 B2 | 6/2013 | Hoffman et al. | |
| 2005/0093709 A1 | 5/2005 | Franco et al. | |
| 2006/0003809 A1* | 1/2006 | Boling | G08B 15/00 455/564 |
| 2006/0273916 A1* | 12/2006 | Ortelle | G08B 15/001 340/574 |
| 2007/0063853 A1* | 3/2007 | Derrick | G01S 5/0054 340/573.4 |
| 2008/0284587 A1 | 11/2008 | Saigh et al. | |
| 2008/0294058 A1 | 11/2008 | Shklarski | |
| 2009/0289807 A1 | 11/2009 | Enwright et al. | |
| 2009/0321291 A1* | 12/2009 | Asla | A45C 11/00 206/320 |
| 2010/0097207 A1 | 4/2010 | Mildenberger et al. | |
| 2010/0098240 A1 | 4/2010 | Ji et al. | |
| 2010/0100319 A1* | 4/2010 | Trinko | G01C 21/367 701/455 |
| 2010/0141391 A1 | 6/2010 | Music et al. | |
| 2010/0285771 A1 | 11/2010 | Peabody | |
| 2011/0059720 A1 | 3/2011 | Penix | |
| 2012/0050046 A1 | 3/2012 | Satorius | |
| 2012/0212339 A1* | 8/2012 | Goldblatt | G08B 25/016 340/539.11 |
| 2012/0270559 A1 | 10/2012 | Ingerson | |
| 2013/0040600 A1 | 2/2013 | Reitnour et al. | |
| 2013/0078942 A1 | 3/2013 | Owens et al. | |
| 2013/0135097 A1* | 5/2013 | Doezema | G08B 21/0446 340/539.13 |
| 2013/0154823 A1* | 6/2013 | Ostrer | G08B 21/18 340/539.1 |
| 2014/0079217 A1* | 3/2014 | Bai | H04L 63/0869 380/270 |
| 2014/0162729 A1* | 6/2014 | Garden | H04B 1/3888 455/566 |
| 2014/0197945 A1 | 7/2014 | Gu et al. | |

OTHER PUBLICATIONS

PCT/US14/20420, International Search Report and Written Opinion, Mailed: Jul. 9, 2014.
Greatcall, 5 Star Urgent Response, www.greatcall.com/FiveStar_urgent_response/, Jul. 4, 2012.
Amazon, GE 51208 SmartHome Personal Security Keychain Alarm, http://www.amazon.com/GE-51208-SmartHome-Personal-Security/dp/B0000YNR5Q%3FSubscription-Id%3DAKIAJFYC2737UW7RPO7Q%26tag%3Dluvlustlies-20%26linkCode%3Dxm2%26camp%3D2025%26creative-%3D165953%26creativeASIN%3DB0000YNR5Q, Nov. 22, 2011.
Boonsri Dickinson, "Jawbone's UP wristband tracks sleep,food, exercise" http://www.zdnet.com/article/jawbones-up-wristband-tracks-sleep-food-exercise/, Nov. 4, 2011.
My Ring Guard, www.myringguard.com/default.asp, Oct. 19, 2012.
Business Line, Security Watch unveils mobile application for women under threat, www.thehindubusinessline.com/industry-and-economy/info-tech/security-watch-unveils-mobile-application-for-women-under-threat/article4245394.ece, Feb. 27, 2012.
U.S. Appl. No. 14/197,058, filed Mar. 4, 2014, Final Office Action mailed Dec. 2, 2015.
U.S. Appl. No. 14/197,058, filed Mar. 4, 2014, Office Action mailed Apr. 2, 2016.
U.S. Appl. No. 14/197,058, Filed Mar. 3, 2014, Final Office Action mailed Sep. 7, 2016.

* cited by examiner

INTERCHANGEABLE PERSONAL SECURITY DEVICE WITH A COMMUNICATION ACCESSORY

CROSS-REFERENCES TO RELATED APPLICATIONS

This is a continuation-in-part application of and claims priority to, U.S. patent application Ser. No. 14/197,058 entitled "AN INTERCHANGEABLE PERSONAL SECURITY DEVICE" and filed on Mar. 4, 2014 for Jacqueline V. Ros, which claims the benefit of U.S. Provisional Patent Application No. 61/851,225 entitled "PERSON TRACKING DEVICE" and filed on Mar. 4, 2013 for Jacqueline V. Ros, U.S. Provisional Patent Application No. 61/827,725 entitled "PERSON TRACKING DEVICE" and filed on May 27, 2013 for Jacqueline V. Ros, and U.S. Provisional Patent Application No. 61/844,138 entitled "INTERCHANGEABLE PERSONAL SECURITY DEVICE" and filed on Jul. 9, 2013 for Jacqueline V. Ros, each of which are incorporated herein by reference.

FIELD

This invention relates to a personal security device and more particularly relates to a personal security device that sends an alert signal in response to being activated by a user.

BACKGROUND

Personal security is a concern in many locations. Often a person is attacked while away from home or a person has a medical emergency. In addition, the person may be unable to use a cellular phone or other communication device to call for help. For example, a person being attacked may not have time to reach for a cell phone, turn on the cell phone, and dial an emergency contact. In addition, a person having a medical emergency may not be in a condition to get to a phone, call for help, or dial a particular number on a phone.

SUMMARY

An apparatus for personal security is disclosed. A system and method also perform the functions of the apparatus. The apparatus includes a portable accessory formed to receive an alerting device. In a certain embodiment, the alerting device may fit within a compartment of the portable accessory, and the portable accessory may include a communication device. The apparatus, in one embodiment, includes an alerting device with an alerting element. The alerting device is interchangeable with a plurality of portable accessories. One or more activation elements are disposed on the portable accessory and formed to activate the alerting device wherein the alerting element sends an alert signal to the communication device in response to receiving an activation signal from the one or more activation elements.

In various embodiments, the communication device may include a satellite communication device, a short wave radio communication device, a two-way radio communication device, and a cellular network communication device. In one embodiment, the alerting device is in communication with the communication device and sends an alert signal to the communication device in response to receiving the activation signal. In another embodiment, the communication device notifies one or more predefined contacts that an alert signal was sent in response to receiving the alert signal.

In one embodiment, the communication device includes a power supply separate from a power supply for the alerting device. In a further embodiment, the power supply for the communication device provides more power than the power supply for the alerting device. In one embodiment, the power supply for the communication device may include a battery. In a further embodiment, the battery may include a rechargeable battery and/or a disposable batter. In another embodiment, the power supply for the communication device may include a fuel cell. In a further embodiment, the fuel cell may be capable of maintaining an isolated fuel supply until the fuel cell is activated.

In a certain embodiment, the communication device is powered on in response to the activation signal. In another embodiment, the apparatus includes an audible/visual alert module that transmits an audible alert and/or a visual alert in response to activating an activation element of the one or more activation elements. In one embodiment, a power supply for the communication device provides power for the audible/visual alert module. In a further embodiment, the alerting element sends the alert signal to the communication device in response to a first activation signal from the one or more activation elements. In a certain embodiment, the audible/visual alert module transmits the audible and/or visual alert in response to a second activation signal from the one or more activation elements. In a further embodiment, the first activation signal may differ from the second activation signal.

A system for personal security includes, in one embodiment, an interchangeable alerting device shaped to fit within two or more portable accessories and an activation module in the alerting device that receives an activation signal in response to a user interacting with one or more activation elements of the alerting device. In a further embodiment, at least one of the portable accessories may include a communication device. The system, in one embodiment, includes an alert module in wireless communication with the communication device that wirelessly sends an alert signal to the communication device in response to receiving the activation signal and a notification module that sends a notification in response to the communication device receiving the alert signal. The communication device sends the notification to one or more predefined contacts.

In one embodiment, the communication device sends the notification to one or more predefined contacts by communicating with a single distribution device that distributes the notification to the one or more predefined contacts. In another embodiment, the system may include a second communication device separate from the portable accessories. In a further embodiment, the second communication device may receive the alert signal and send a notification to one or more additional predefined contacts.

In one embodiment, the system includes a map module that displays a recommended safe route between origin and destination points. In a further embodiment, the map module may determine the recommended safe route based on lighting, open businesses, and/or reported crime. In a certain embodiment, the system includes a security notification module that sends a notification to a security force in response to the communication device receiving the alert signal. In a further embodiment, the notification to the security force may include the location of the user. In one embodiment, the system includes an automotive notification module that sends a notification via an automobile communication service, in response to the alert signal.

In one embodiment, the system includes a contacts module that stores the one or more predefined contacts and organizes the one or more predefined contacts into one or more groups. In another embodiment, the system includes a location module that sends a location of the user in response to the communication device receiving the alert signal.

A method for personal security includes receiving, in an alerting device, an activation signal in response to a user interacting with one or more activation elements of the alerting device. The alerting device is interchangeable and is shaped to fit within two or more portable accessories. At least one of the portable accessories may include a communication device. The method, in one embodiment, includes wirelessly sending an alert signal to the communication device in response to receiving the activation signal. The communication device is in communication with the alerting device. In one embodiment, the method includes sending a notification in response to the communication device receiving the alert signal. The communication device sends the notification to one or more predefined contacts.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION

Figure 1A:
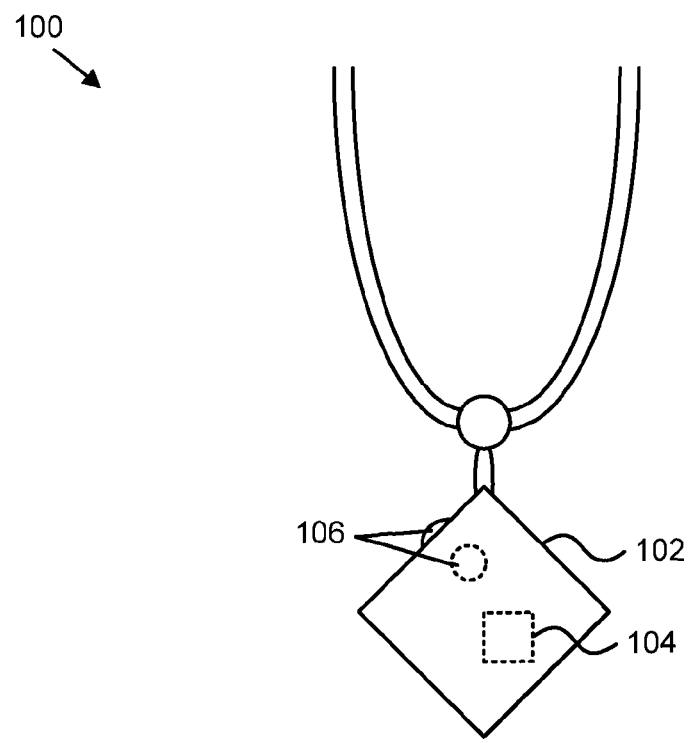
FIG. 1A is a perspective view illustrating one embodiment of an interchangeable personal security device.

Reference throughout this specification to "one embodiment," "an embodiment," or similar language means that a particular feature, structure, or characteristic described in connection with the embodiment is included in at least one embodiment. Thus, appearances of the phrases "in one embodiment," "in an embodiment," and similar language throughout this specification may, but do not necessarily, all refer to the same embodiment, but mean "one or more but not all embodiments" unless expressly specified otherwise. The terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Furthermore, the described features, advantages, and characteristics of the embodiments may be combined in any suitable manner. One skilled in the relevant art will recognize that the embodiments may be practiced without one or more of the specific features or advantages of a particular embodiment. In other instances, additional features and advantages may be recognized in certain embodiments that may not be present in all embodiments.

These features and advantages of the embodiments will become more fully apparent from the following description and appended claims, or may be learned by the practice of embodiments as set forth hereinafter. As will be appreciated by one skilled in the art, aspects of the present invention may be embodied as a system, method, and/or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module," or "system." Furthermore, aspects of the present invention may take the form of a computer program product embodied in one or more computer readable medium(s) having program code embodied thereon.

Many of the functional units described in this specification have been labeled as modules, in order to more particularly emphasize their implementation independence. For example, a module may be implemented as a hardware circuit comprising custom VLSI circuits or gate arrays, off-the-shelf semiconductors such as logic chips, transistors, or other discrete components. A module may also be implemented in programmable hardware devices such as field programmable gate arrays, programmable array logic, programmable logic devices or the like.

Modules may also be implemented in software for execution by various types of processors. An identified module of program code may, for instance, comprise one or more physical or logical blocks of computer instructions which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of program code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different storage devices, and may exist, at least partially, merely as electronic signals on a system or network. Where a module or portions of a module are implemented in software, the program code may be stored and/or propagated on in one or more computer readable medium(s).

The computer readable medium may be a tangible computer readable storage medium storing the program code. The computer readable storage medium may be, for example, but not limited to, an electronic, magnetic, optical, electromagnetic, infrared, holographic, micromechanical, or semiconductor system, apparatus, or device, or any suitable combination of the foregoing.

More specific examples of the computer readable storage medium may include but are not limited to a portable computer diskette, a hard disk, a random access memory (RAM), a read-only memory (ROM), an erasable programmable read-only memory (EPROM or Flash memory), a portable compact disc read-only memory (CD-ROM), a digital versatile disc (DVD), an optical storage device, a magnetic storage device, a holographic storage medium, a micromechanical storage device, or any suitable combination of the foregoing. In the context of this document, a computer readable storage medium may be any tangible medium that can contain, and/or store program code for use by and/or in connection with an instruction execution system, apparatus, or device.

The computer readable medium may also be a computer readable signal medium. A computer readable signal medium may include a propagated data signal with program code embodied therein, for example, in baseband or as part of a carrier wave. Such a propagated signal may take any of a variety of forms, including, but not limited to, electrical, electro-magnetic, magnetic, optical, or any suitable combination thereof. A computer readable signal medium may be any computer readable medium that is not a computer readable storage medium and that can communicate, propagate, or transport program code for use by or in connection with an instruction execution system, apparatus, or device. Program code embodied on a computer readable signal medium may be transmitted using any appropriate medium, including but not limited to wire-line, optical fiber, Radio Frequency (RF), or the like, or any suitable combination of the foregoing In one embodiment, the computer readable medium may comprise a combination of one or more computer readable storage mediums and one or more computer readable signal mediums. For example, program code may be both propagated as an electro-magnetic signal through a fiber optic cable for execution by a processor and stored on RAM storage device for execution by the processor.

Program code for carrying out operations for aspects of the present invention may be written in any combination of one or more programming languages, including an object oriented programming language such as Java, Smalltalk, C++, PHP or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The computer program product may be shared, simultaneously serving multiple customers in a flexible, automated fashion. The computer program product may be standardized, requiring little customization and scalable, providing capacity on demand in a pay-as-you-go model. The computer program product may be stored on a shared file system accessible from one or more servers.

The computer program product may be integrated into a client, server and network environment by providing for the computer program product to coexist with applications, operating systems and network operating systems software and then installing the computer program product on the clients and servers in the environment where the computer program product will function.

In one embodiment software is identified on the clients and servers including the network operating system where the computer program product will be deployed that are required by the computer program product or that work in conjunction with the computer program product. This includes the network operating system that is software that enhances a basic operating system by adding networking features.

Furthermore, the described features, structures, or characteristics of the embodiments may be combined in any suitable manner. In the following description, numerous specific details are provided, such as examples of programming, software modules, user selections, network transactions, database queries, database structures, hardware modules, hardware circuits, hardware chips, etc., to provide a thorough understanding of embodiments. One skilled in the relevant art will recognize, however, that embodiments may be practiced without one or more of the specific details, or with other methods, components, materials, and so forth. In other instances, well-known structures, materials, or operations are not shown or described in detail to avoid obscuring aspects of an embodiment.

Aspects of the embodiments are described below with reference to schematic flowchart diagrams and/or schematic block diagrams of methods, apparatuses, systems, and computer program products according to embodiments of the invention. It will be understood that each block of the schematic flowchart diagrams and/or schematic block diagrams, and combinations of blocks in the schematic flowchart diagrams and/or schematic block diagrams, can be implemented by program code. The program code may be provided to a processor of a general purpose computer, special purpose computer, sequencer, or other programmable data processing apparatus to produce a machine, such that the instructions, which execute via the processor of the computer or other programmable data processing apparatus, create means for implementing the functions/acts specified in the schematic flowchart diagrams and/or schematic block diagrams block or blocks.

The program code may also be stored in a computer readable medium that can direct a computer, other programmable data processing apparatus, or other devices to function in a particular manner, such that the instructions stored in the computer readable medium produce an article of manufacture including instructions which implement the function/act specified in the schematic flowchart diagrams and/or schematic block diagrams block or blocks.

The program code may also be loaded onto a computer, other programmable data processing apparatus, or other devices to cause a series of operational steps to be performed on the computer, other programmable apparatus or other devices to produce a computer implemented process such that the program code which executed on the computer or other programmable apparatus provide processes for implementing the functions/acts specified in the flowchart and/or block diagram block or blocks.

The schematic flowchart diagrams and/or schematic block diagrams in the Figures illustrate the architecture, functionality, and operation of possible implementations of apparatuses, systems, methods and computer program products according to various embodiments of the present invention. In this regard, each block in the schematic flowchart diagrams and/or schematic block diagrams may represent a module, segment, or portion of code, which comprises one or more executable instructions of the program code for implementing the specified logical function(s).

It should also be noted that, in some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. Other steps and methods may be conceived that are equivalent in function, logic, or effect to one or more blocks, or portions thereof, of the illustrated Figures.

Although various arrow types and line types may be employed in the flowchart and/or block diagrams, they are understood not to limit the scope of the corresponding embodiments. Indeed, some arrows or other connectors may be used to indicate only the logical flow of the depicted embodiment. For instance, an arrow may indicate a waiting or monitoring period of unspecified duration between enumerated steps of the depicted embodiment. It will also be noted that each block of the block diagrams and/or flowchart diagrams, and combinations of blocks in the block diagrams and/or flowchart diagrams, can be implemented by special purpose hardware-based systems that perform the specified functions or acts, or combinations of special purpose hardware and program code.

Descriptions of Figures may refer to elements described in previous Figures, like numbers referring to like elements. FIGS. 1A through 1E depict various embodiments of an interchangeable personal security device 100, 110, 120, 140, 150, including a portable accessory 102, 112, 122, 142, 152. In certain embodiments, as depicted in FIGS. 1A through 1D, the portable accessory 102, 112, 122, 142 may be a wearable accessory. In another embodiment, as depicted in FIG. 1E, the portable accessory 152 may not be wearable. FIG. 1A depicts one embodiment of an interchangeable personal security device 100. In one embodiment, the interchangeable personal security device 100 includes a portable or wearable accessory 102, an alerting device 104, and one or more activation elements 106, which are described below.

The wearable accessory 102, in one embodiment, has an aesthetically pleasing appearance. In certain embodiments, the wearable accessory 102 includes the appearance of jewelry, such as a necklace, amulet, bracelet, ring, or the like. In other embodiments, the wearable accessory 102 includes a watch, sunglasses, a pin, a brooch, a belt buckle, or the like. In certain embodiments, the wearable accessory 102 includes various sportswear accessories, such as athletic watches, fitness bands, sweatbands, wristbands, or the like. In some embodiments, the wearable accessory 102 clips-on to an article of clothing, such as a shoelace, zipper, collar, pocket, bra, belt, hat, purse, or the like. In one embodiment, the wearable accessory 102 includes a substantially rigid body. The substantially rigid body may include various materials, such as plastic, metal, precious metal, crystals, gems, jewels, or the like, or any combination of the aforementioned materials. For example, the wearable accessory 102 may be a necklace with an attached pendant where the pendant includes a metal body with an embedded jewel. In one embodiment, the wearable accessory 102 includes waterproof material.

In certain embodiments, the wearable accessory 102 is formed to receive an alerting device 104, which is described in more detail below. The wearable accessory 102, in another embodiment, receives the alerting device 104 such that the alerting device 104 is not visible while the wearable accessory 102 is worn. For example, the alerting device 104 may be located within the wearable accessory 102. In such an embodiment, the wearable accessory 102 includes a casing that covers and protects the alerting device 104. Furthermore, such an embodiment may be water resistant, such that portions of the wearable accessory 102 are connected in a way to prevent water from penetrating the wearable accessory 102 and damaging the alerting device 104. In other embodiments, the alerting device 104 may be disposed on a portion of the wearable accessory 102 that is not visible while being worn. For example, the alerting device 104 may be disposed along the backside of a watch such that it is not visible while the watch is worn.

In another embodiment, the alerting device 104 includes an alerting element. In one embodiment, the alerting element sends an alert signal in response to receiving an activation signal. In some embodiments, the alert signal is a silent alarm, which may be received by an external device without alerting those near the alerting device 104 that an alarm has been triggered. In another embodiment, the alert signal is a loud alarm that emits an audible alarm signal, such as a siren or similar noisemaker, intended to warn and/or alert persons near the alerting device 104. For example, a person who feels threatened by another person may trigger a loud alarm to scare the person and/or to alert others. In some embodiments, the alerting device 104 includes both silent and loud alarms. For example, the loud alarm may be triggered by the user separately from a silent alarm. In another embodiment, the loud alarm includes sending an alert to a communication device.

In one embodiment, the alerting device 104 is interchangeable with a plurality of portable or wearable accessories 102. For example, a single alerting device 104 may be used in a watch, a pendant, a bracelet, a brooch, a ring, or the like. In one embodiment, at least one of the portable accessories 102 may include a communication device as described with regard to FIG. 1E. In various embodiments, an alerting device 104 may be in communication with a communication device that is included with a portable accessory 102, or may be in communication with a separate communication device, not included with a portable or wearable accessory 102. In some embodiments, using an interchangeable alerting device 104 allows a user to customize wearable accessories 102 without providing multiple alerting devices 104. The alerting device 104, in another embodiment, includes different shapes and sizes to accommodate different wearable accessories 102. For example, the alerting device 104 may be compact enough to fit in a charm, a ring, or the like.

In some embodiments, the alerting device 104 is permanently connected to the wearable accessory 102, such that it is not interchangeable with other wearable accessories. For example, an alerting device 104 may be permanently built into a watch, such that the alerting device 104 is not designed to be removed, but is instead operationally connected to the watch. In some embodiments, the watch includes different personal security features, which would not function without the alerting device 104 installed.

In certain embodiments, the one or more activation elements 106 are disposed on the wearable accessory 102 and are formed to activate the alerting device 104. In one embodiment, the activation elements 106 include buttons, switches, or the like. In certain embodiments, the activation elements 106 are flush mounted with the surface of the wearable accessory 102 such that they do not protrude past the surface of the wearable accessory 102. In other embodiments, the activation elements 106 are shaped to accommodate a user's finger or hand and may protrude past the surface of the wearable accessory 102. In one embodiment, the activation elements 106 include the same material as the wearable accessory 102, such as plastic, metal, or the like. In other embodiments, the activation elements 106 may include a substantially flexible material, such as rubber, soft plastic, or the like.

Even though the illustrated embodiment depicts a wearable accessory 102 having two activation elements 106, any number of activation elements 106 may be used to activate the alerting device 104, the wearable accessory 102, and/or different personal security preferences. In some embodiments, the activation elements 106 are not visible while the wearable accessory 102 is being worn. For example, the activation elements 106 may be located on the backside of a watch or a pendant, which may not be visible while the accessory 102 is being worn. In another embodiment, the activation elements 106 are integrated into elements of the wearable accessory 102 such that the activation elements 106 appear to be part of the design of the wearable accessory 102. For example, a button on a watch that appears to be a button that adjusts a setting of the watch may in fact be an activation button. Similarly, a gem stone on a ring may actually be an activation element that a user pushes, twists, or the like, to activate the alerting device 104 and/or the wearable accessory 102. In some embodiments that include more than one activation element 106, only one activation element 106 may be pressed at one time. In other embodiments, two or more activation elements 106 may be pressed at the same time. In some embodiments, the one or more activation elements 106 turn on one or more light sources, such as a light-emitting diode ("LED"), disposed on the wearable accessory 102.

In certain embodiments, the wearable accessory 102 also includes an electronic power source (not shown) to power the communication functions of the alerting device 104. In some embodiments, the electronic power source includes a disposable battery, which is designed to be used once and discarded. In another embodiment, the electronic power source includes a rechargeable battery, which is designed to be recharged and used multiple times. In certain embodiments, the rechargeable battery may be charged using a power outlet, a computer (e.g., via a USB port), an induction charging system, or the like.

In one embodiment, the wearable accessory 102 includes its own power source that is separate from the power source that powers the alerting device 104, such as a battery. In another embodiment, the wearable accessory 102 and the alerting device 104 share a power source. In some embodiments, the wearable accessory 102 includes functionality separate from the alerting device 104, which may require power from the power source. For example, the wearable accessory 102 may include communications functionality, such as cell phone service, Bluetooth®, Wi-Fi, and/or the like. Alternatively, the wearable accessory 102 may include functionality for location services (e.g., a global positioning system ("GPS")), an alarm, and/or the like. Thus, the wearable accessory 102 may perform one or more personal security functions without using the alerting device 104.

In some embodiments, non-battery power sources may be used in conjunction with and/or in addition to a battery source. In another embodiment, non-battery power sources are used to recharge a battery source. In one embodiment, the wearable accessory 102 includes a power source that derives its power from the kinesthetic movements of the wearer. For example, the wearable accessory 102 may be a watch that is powered through the arm movements of the wearer. In another embodiment, the wearable accessory 102 includes a power source that derives its power from a solar panel disposed on the wearable accessory 102 such that the wearable accessory 102 is powered when exposed to sunlight. In a further embodiment, the wearable accessory 102 may include a fuel cell that provides power to the wearable accessory 102. In one embodiment, the power source is not used until an activation signal is received to activate the alerting device 104. In some embodiments, the alerting device 104 is constantly monitoring and drawing power from the power source.

Figure 1B:
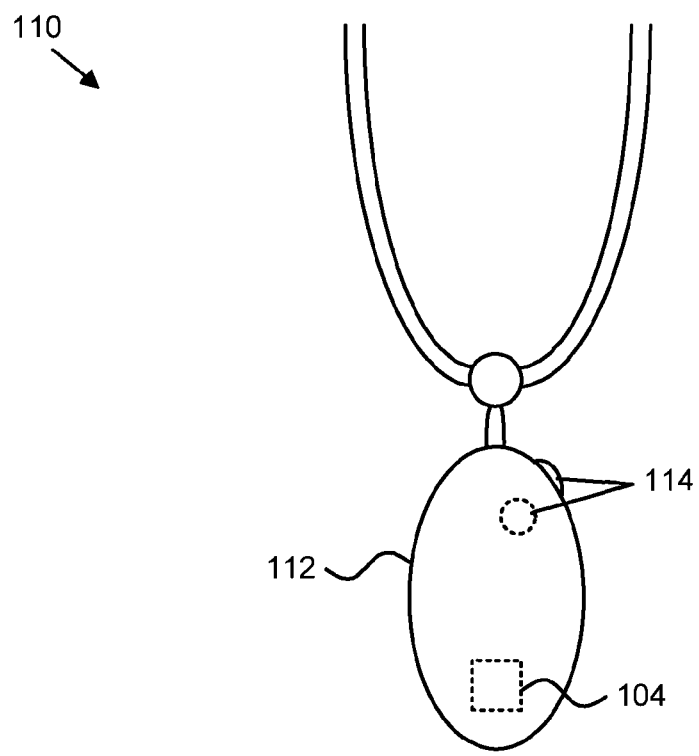
FIG. 1B is a perspective view illustrating another embodiment of an interchangeable personal security device.

FIG. 1B depicts another embodiment of an interchangeable personal security device 110. The interchangeable personal security device 110 includes elements that are substantially similar to the interchangeable personal security device 100 of FIG. 1A. In one embodiment, FIG. 1B depicts the alerting device 104 being interchangeable in a different wearable accessory 112. For example, the user may wear an interchangeable personal security device 100 that includes a necklace having a wearable accessory 102 in the form of a diamond shaped pendant and also an interchangeable personal security device 110 that includes a necklace having a wearable accessory 112 in the form of an oval shaped pendant. The alerting device 104 may be interchangeable in both devices 100, 110. In certain embodiments, the alerting device 104 is interchangeable regardless the placement of the activation elements 106, 114. In this manner, a user may customize the wearable accessories 102 associated with an alerting device 104 without having to reconfigure multiple wearable accessories 102.

Figure 1C:
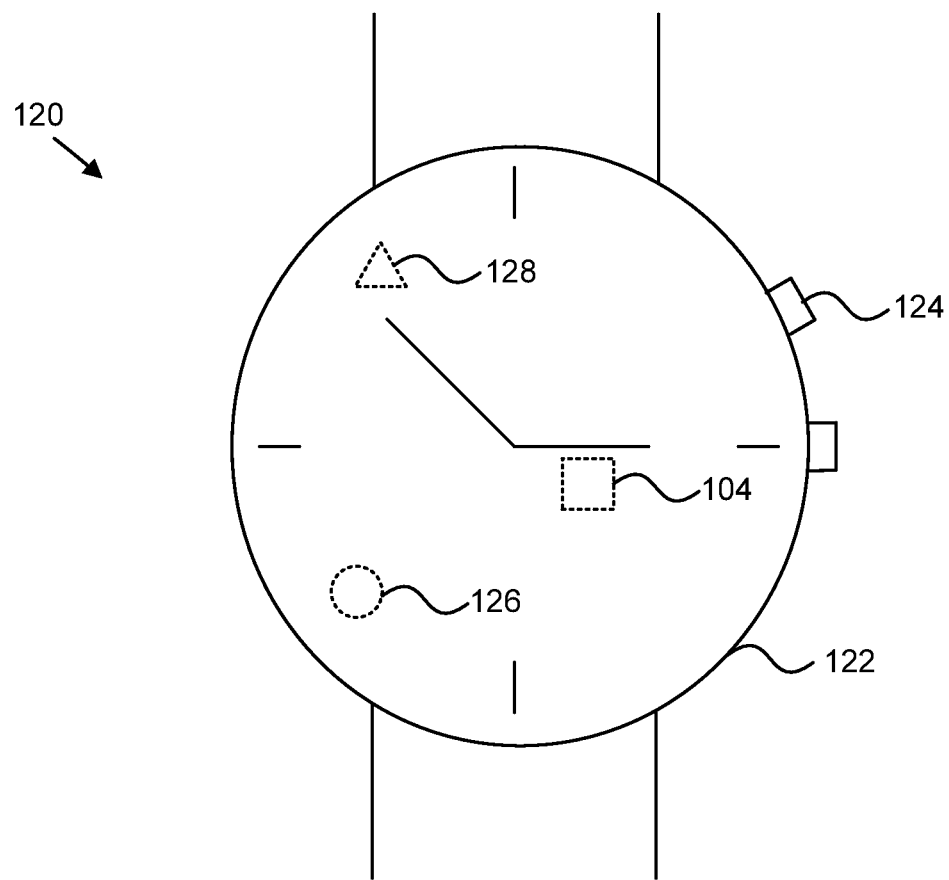
FIG. 1C is a perspective view illustrating a further embodiment of an interchangeable personal security device.

FIG. 1C depicts one embodiment of an interchangeable personal security device 120. In the depicted embodiment, the interchangeable personal security device may include a wearable accessory 102 that is embodied as a watch 122. The watch 122 may include one or more buttons that control the settings of the watch, such as setting the time, date, or the like. In some embodiments, a button 124 may appear to be a functioning part of the design of the watch 122; however, the button 124 may activate one or more personal security components of the watch 122. For example, the watch 122 may include one or more of an alarm component 126, which may trigger a loud or silent alarm, a cellular communication component 128, which may communicate with one or more communications devices over a cellular network, or the like, in addition to an alerting device 104. Other personal security components may include a location services component (e.g., GPS), a Bluetooth® component, a Wi-Fi component, or the like.

In response to a user interacting with the button 124, the alerting device 104 may be activated. Alternatively, if the alerting device 104 is out of range of a communication device that is configured to receive an alert signal from the alerting device 104, one or more different personal security components may become activated, such as the alarm component 126, the cellular communication component 128, or the like. The watch 122 may include a plurality of power sources configured to power the personal security elements 104, 126, 128. For example, the alerting device 104 may be powered by a battery while the cellular communication component 128 is powered by a different battery. Moreover, in addition to the alerting device 104 being interchangeable with different wearable accessories 122, the other personal security components 126, 128 may also be interchangeable. Some wearable accessories 102 compatible with the altering device 104 may include a separate power source and may include functionality in addition to the altering device 104 while other wearable accessories 102 compatible with the same alerting device 104 may not have a separate power source so that any additional functionality, such as cellular or GPS capabilities, alarm power, etc., may be powered by the alerting device 104 or may not have additional functionality.

Figure 1D:
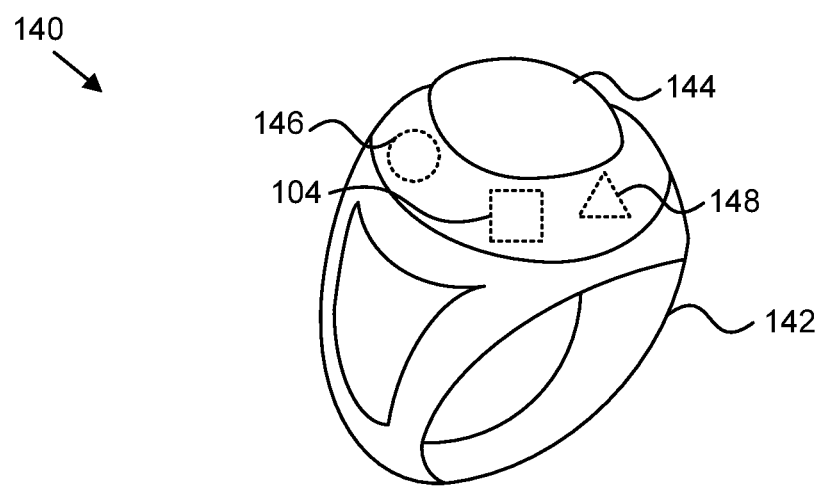
FIG. 1D is a perspective view illustrating another embodiment of an interchangeable personal security device.
Figure 1E:
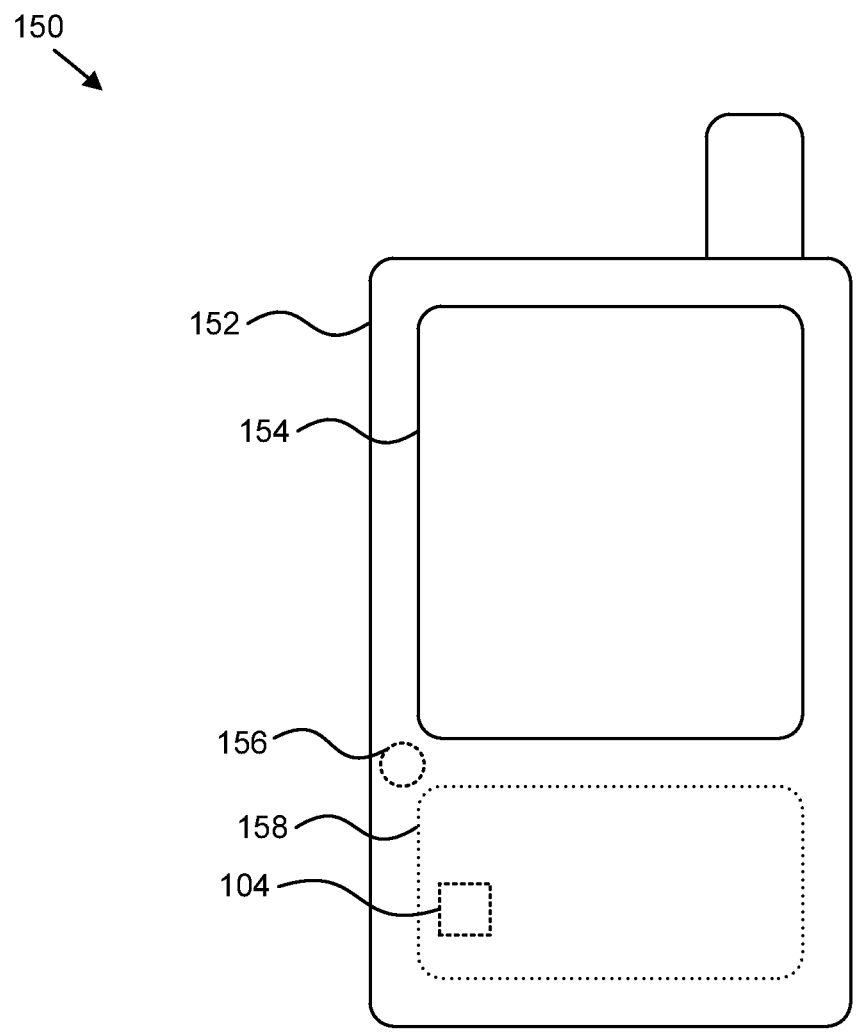
FIG. 1E is a perspective view illustrating another embodiment of an interchangeable personal security device.

FIG. 1D depicts another embodiment of an interchangeable personal security device 140. In the depicted embodiment, the wearable accessory 102 includes a ring 142. The ring 142 may include a gem, jewel, or the like that comprises the activation button 144 for the device. Thus, in the depicted embodiment, the activation button 144 is discrete because it appears to be a design feature of the ring 142 instead of a button 144. Similar to the watch 122 in FIG. 1C, the ring 142 includes an alerting device 104 and other personal security components, such as an alarm component 146 and a cellular communication component 148, which may be substantially similar to the personal security components 126, 128 of FIG. 1C.

In some embodiments, in response to the activation button 144 being interacted with, the alerting device 104 may be activated and may send an alarm signal to an external communications device. In some embodiments, however, if the alerting device 104 is taken out of the communications range of the alerting device 104 and/or the communications device, the other personal security components 146, 148 of the ring 142 may be activated. Further, like the watch 122 of FIG. 1C, the ring 142 may also include a plurality of power sources to power the different personal security components 104, 146, 148.

FIG. 1E depicts another embodiment of an interchangeable personal security device 150. In the depicted embodiment, a portable accessory 102 comprises a communication device 152. The portable accessory 102 is formed to receive the alerting device 104, such that the alerting device 104 fits within a compartment 158 of the portable accessory 102. For example, in one embodiment, the portable accessory 102 may be a shell that includes a compartment 158 for the alerting device 104, and that encloses a communication device 152. In another embodiment, the portable accessory 102 may be a communication device 152 with a compartment 158 for the alerting device 104.

In the depicted embodiment, the communication device 152 includes a touch screen 154 with controls. In another embodiment, the communication device may include buttons or other types of controls. In certain embodiments, the controls for the communication device 152 may include one or more activation elements for the alerting device 104. Thus, in various embodiments, the alerting device 104 may be activated by pressing a button, pressing a sequence of buttons, activating an app on the communication device 152, or the like. In the depicted embodiment, the communication device 152 includes an alarm component 156, which may, in some embodiments be similar to the alarm component 126 of FIG. 1C.

In some embodiments, an alerting device 104 in a portable accessory 102, 112, 122, 142, 152 may be in wireless communication with a separate communication device, such as a cellular phone. In certain environments, such as urban settings, a cellular telephone may provide adequate communication capabilities for providing personal security. However, in other environments, such as rural or backcountry environments with poor cellular reception, a different type of communication device 152 may provide better communication capabilities for personal security. Because many users do not ordinarily carry a communication device other than a cellular phone, a portable accessory 102 that includes the communication device 152 may allow a user to use different forms of communication when cellular reception is poor. Thus, in various embodiments, the communication device 152 may include a satellite communication device, such as a satellite phone, a short wave radio communication device, such as an amateur or citizens band radio, a two-way radio communication device such as a walkie-talkie, a cellular network communication device such as a cell phone, or the like.

For example, the communication device 152 may be configured specifically for use with the alerting device 104 and may have less functionality than a typical satellite phone, two-way radio, etc. and thus may be less expensive than a fully functional satellite phone, two-way radio. In other embodiments, the communication device 152 may have capabilities of a typical satellite phone, two-way radio, etc. but may have additional capabilities associated with adding the alerting device 104. For example, adding the alerting device 104 may add one-touch emergency notification. One of skill in the art will recognize other capabilities of a communication device 152 with an alerting device 104.

In certain embodiments, the alerting device 104 may be in wireless communication with the communication device 152. In another embodiment, the compartment 158 for the alerting device 104 may include a wired connection to the communication device 152. In one embodiment, the communication device 152 may include a power supply separate from a power supply for the alerting device 104. In certain embodiments, an alerting device 104 that is interchangeable with a plurality of portable accessories may have small, low-power power supply, so that the alerting device 104 can fit interchangeably into small wearable accessories. However, communication from backcountry areas may involve a larger, higher-power power supply. Thus, in certain embodiments, the power supply for the communication device 152 may provide more power than the power supply for the alerting device 104.

In one embodiment, the power supply for the communication device may include a battery, such as a rechargeable battery, a disposable battery, or the like. In another embodiment, the power supply for the communication device may include a fuel cell. In a further embodiment, the fuel cell may be capable of maintaining an isolated fuel supply until the fuel cell is activated. For example, a zinc-air fuel cell (sometimes referred to as a zinc-air battery) may include a seal that isolates zinc from air, so that the zinc fuel does not react until the fuel cell is activated by breaking or removing the seal. In various embodiments, isolating the fuel supply for a fuel cell may provide a shelf-stable power supply that is ready for use when activated, without a user frequently checking or replacing batteries.

In one embodiment, the communication device 152 may be powered on in response to receiving an activation signal from the alerting device 104. Prior to receiving the activation signal, the communication device 152 may be in a powered-off state, or a low-power standby state. For example, in one embodiment, a fuel cell with an isolated fuel supply may be activated (so that the fuel supply can react and provide power) in response to the activation signal. In some embodiments, a communication device 152 that is powered on in response to an activation signal may be less convenient than an always-on communication device such as a phone. However, in certain embodiments, it may be impractical to regularly recharge or refresh a power supply for a communication device. For example, a personal security device 150 for backcountry medical emergencies may be regularly carried without an emergency occurring, and may stay powered off (or keep an isolated fuel supply) so that it is ready to be activated if an emergency occurs.

Figure 2:
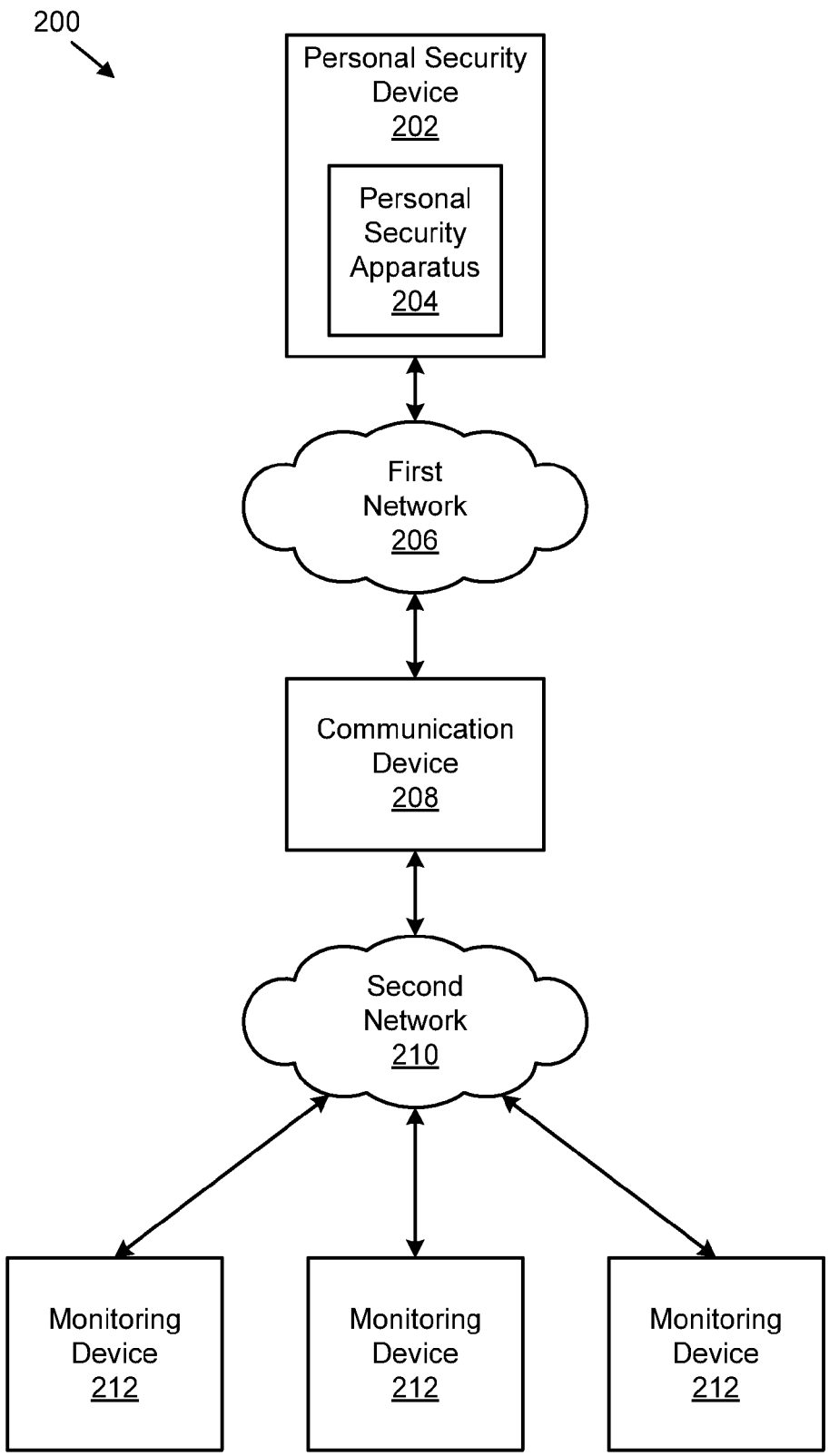
FIG. 2 is a schematic block diagram illustrating one embodiment of a system for an interchangeable personal security device.

FIG. 2 depicts one embodiment of a system 200 for an interchangeable personal security device. The system 200, in one embodiment, includes an interchangeable personal security device 202, a personal security apparatus 204, and a first network 206. In a further embodiment, the system 200 includes a communication device 208, a second network 210, and one or more monitoring devices 212, which are described below in more detail.

The system 200, in one embodiment, includes an interchangeable personal security device 202, which may be substantially similar to the interchangeable personal security devices 100, 110, 120, 140, 150 described above. The interchangeable personal security device 202, in certain embodiments, is a portable or wearable accessory 102, 112, 122, 142, 152 that includes an alerting device 104 and one or more activation elements 106, 114, as described above with reference to FIGS. 1A-1E. In another embodiment, the alerting device 104 is interchangeable with different portable or wearable accessories 102, 112, 122, 142, 152 such as a pendant, watch, ring, communication accessory, or the like. Hereinafter, a portable or wearable accessory may take any form, such as the wearable accessories 102, 112, 122, and 142, as depicted in FIGS. 1A-1D, or the portable accessory including a communication device 152 as depicted in FIG. 1E, but for simplicity is referred to as "portable accessory 102."

In one embodiment, the system 200 includes a personal security apparatus 204. The personal security apparatus 204, in another embodiment, is configured to activate the interchangeable personal security device 202 and send an alert signal to a communication device 208 over a first network 206. The personal security apparatus 204 is described in more detail below with reference to FIGS. 3 and 4. The personal security apparatus 204 may be included in the alerting device 104 or may be distributed between the alerting device and the portable accessory 102.

The system 200, in certain embodiments, includes a first network 206. The first network 206, in certain embodiments, is a digital communication network that transmits digital communications related to an interchangeable personal security device 202. The first network 206 may include a wireless network, such as a wireless telephone network, a local wireless network, such as a Wi-Fi network, a Bluetooth® network, an ANT+™ wireless connection, a near field communication ("NFC") connection, and the like. The first network 206 may include a wide area network ("WAN"), a storage area network ("SAN"), a local area network ("LAN"), an optical fiber network, the internet, or other digital communication network known in the art. The first network 206 may include two or more networks. The first network 206 may include one or more servers, routers, switches, and/or other networking equipment. The first network 206 may also include computer readable storage media, such as a hard disk drive, an optical drive, non-volatile memory, random access memory ("RAM"), or the like.

In a further embodiment, the system 200 includes a communication device 208. The communication device 208, in one embodiment, includes a cell phone, a smart phone, a tablet computer, a laptop computer, a desktop computer, a smart TV, an e-book reader, a PDA, a Global Positioning System ("GPS") device, or the like. In certain embodiments, the communication device 208 communicates with the interchangeable personal security device 202 using the first network 206. In another embodiment, the communication device 208 is directly connected to the personal security device 202 via a wired or wireless link. In one embodiment, a plurality of interchangeable personal security devices 202 is in communication with a single communication device 208. For example, each family member in a family of four may have an interchangeable personal security device 202 such that each interchangeable personal security device 202 may be in communication with a single communication device 208.

In one embodiment, the communication device 208 may be included in a portable accessory 102 with a compartment 158 for the personal security device 202. In another embodiment, the communication device 208 may be separate from the portable accessory 102. In a further embodiment, the personal security device 202 may be in communication with a first communication device 208 included in a portable accessory 208 and a second communication device 208, separate from a portable accessory 208, and either or both communication devices 208 may receive an alert signal from the personal security device 202 and send a notification to predefined contacts. For example, a first communication device 208 may send a notification to a first set of predefined contacts, and a second communication device 208 may send a notification to one or more additional predefined contacts.

In some embodiments, the communication device 208 communicates with one or more monitoring devices 212 using the second network 210, which are described below. In certain embodiments, the first network 206 and the second network 210 are the same network. In one embodiment, the first network 206 and the second network 210 share at least a portion of the components that include the first network 206 and second network 210. In another embodiment, the communication device 208 executes a computer program product, such as an application, that is in communication with the interchangeable personal security device 202 and the one or more monitoring devices 212.

The system 200, in one embodiment, includes a second network 210, which may be substantially similar to the first network 206. In some embodiments, the second network 210 is a digital communication network that transmits digital communications between a communication device 208 and one or more monitoring devices 212. The second network 210 may include a wireless network, such as a cellular telephone network, a local wireless network, such as a Wi-Fi network, a Bluetooth® network, a near field communication ("NFC") connection, and the like. The second network 210 may include a wide area network ("WAN"), a storage area network ("SAN"), a local area network ("LAN"), an optical fiber network, the internet, or other digital communication network known in the art. The second network 210 may include two or more networks. The second network 210 may include one or more servers, routers, switches, and/or other networking equipment. The second network 210 may also include computer readable storage media, such as a hard disk drive, an optical drive, non-volatile memory, random access memory ("RAM"), or the like.

In another embodiment, the system 200 includes one or more monitoring devices 212. The one or more monitoring devices 212, in one embodiment, include a cell phone, a smart phone, a tablet computer, a laptop computer, a desktop computer, a smart TV, an e-book reader, a GPS device, a PDA, or the like. In one embodiment, the one or more monitoring devices 212 are in communication with the communication device 208 using the second network 210. In another embodiment, the one or more monitoring devices 212 are in communication with the interchangeable personal security device 202 using a first network 206 and/or a second network 210.

In the depicted embodiment, the communication device 208 may communicate directly with multiple monitoring devices 212 via the second network 210. However, in another embodiment, the communication device 208 may send a notification to multiple predefined contacts or monitoring devices 212 by communicating with a single distribution device that distributes the notification to the multiple predefined contacts or monitoring devices 212. For example, a satellite communication device 208 may communicate with a server over a second network 210 that includes a satellite link, and the server may distribute notifications to multiple monitoring devices 212 over a third network.

Figure 3:
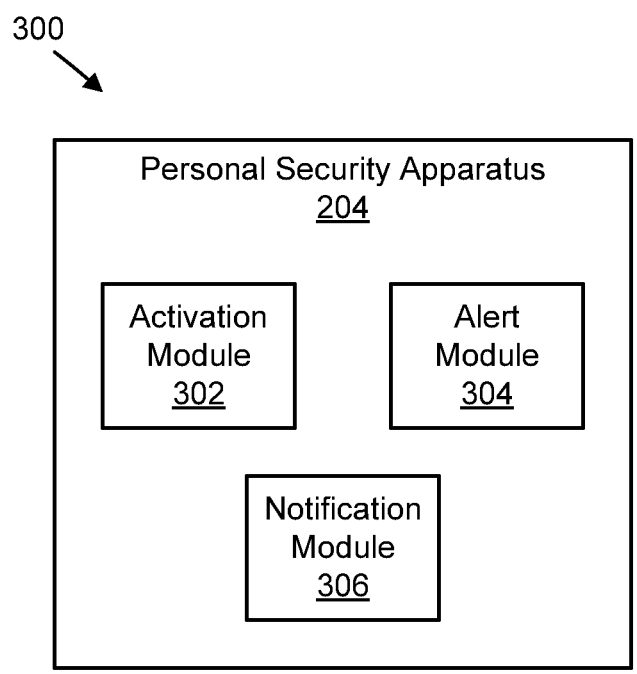
FIG. 3 is a schematic block diagram illustrating one embodiment of an interchangeable personal security apparatus.

FIG. 3 depicts one embodiment an apparatus 300 that includes one embodiment of a personal security apparatus 204. The personal security apparatus 204, in certain embodiments, includes an activation module 302, an alert module 304, and a notification module 306, which are described in more detail below.

In one embodiment, the personal security apparatus 204 includes an activation module 302 configured to receive an activation signal in response to a user interacting with one or more activation elements 106, 114. In one embodiment, the activation module 302 receives an activation signal in response to a single activation element 106, 114 being actuated by the user. In another embodiment, the activation signal receives an activation signal in response to a plurality of activation element 106, 114 being actuated by the user. For example, the activation module 302 may receive an activation signal in response to one button being pressed and/or two or more buttons being pressed at the same time.

In one embodiment, the activation module 302 receives an activation signal in response to a plurality of activation elements 106, 114 being actuated in a specific sequence. For example, an interchangeable personal security device 202 may include three buttons, which, when pressed in a certain order (e.g., left, right, middle), sends an activation signal. In another embodiment, the activation module 302 receives an activation signal in response to the amount of time the one or more activation elements 106, 114 are actuated. For example, the activation module 302 may receive an activation signal in response to the one or more activation elements 106, 114 being pressed and released quickly. In another example, the activation module 302 receives a different activation signal in response to the one or more activation elements 106, 114 being held down for a longer period of time.

In one example, where the personal security apparatus 204 includes more than one activation element 106, 114, each activation element 106, 114 may have a different function. For example, the activation module 302 may receive an activation signal from one activation element 106, 114 while other activation elements 106, 114 may have different functions, like activating an audible alarm, activating a visual alarm, turning on a light, etc. In another embodiment, the activation module 302 may receive an activation signal from one activation element 106, 114 for one purpose and may receive a different activation signal from another activation element 106 for another activation element 106.

In one embodiment, the interchangeable personal security device 202 includes voice activation elements (e.g., a microphone) such that the activation module 302 receives an activation signal in response to the user speaking a phrase, a word, or the like. For example, the user may say "Help!," which may be identified by the activation module 302 as a recognizable activation word. In some embodiments, the activation module 302 may be programmed to recognize other activation words, phrases, or the like. In another embodiment, the activation module 302 may be programmed to recognize one or more persons' voices, such that the interchangeable personal security device 202 may only be activated in response to identifying an activation word or phrase spoken by a recognizable person. In one embodiment, the voice activation capabilities of the activation module 302 may be enabled in response to a user actuating one or more of the activation elements 106, 114. For example, a user may hold down a button to activate the voice recognition capabilities of the activation module 302 while simultaneously speaking an activation word, phrase, or the like.

The personal security apparatus 204, in another embodiment, includes an alert module 304 in wireless communication with a communication device 208 using the first network 206. In certain embodiments, the alert module 304 is configured to wirelessly send an alert signal to the communication device 208 in response to the activation module 302 receiving the activation signal. For example, the alert module 304 may send a silent alarm to the communication device 208, which, as described below, may notify one or more persons, emergency organizations, or the like, that an alarm has been triggered. In one embodiment, the alert module 304 is in communication with a computer program product executing on the communication device 208, such as a personal security application running on a smart device. In other embodiments, the alert module 304 is in communication with a communication device 208 running a network application, such as a web browser, which may send a notification to an online account managed by the user. For example, the alert module 304 may send an alert signal to a laptop computer running a program that is connected to the user's account online, which would define where to forward a notification.

In certain embodiments, the alert module 304 activates an audible alarm in response to receiving an activation signal. For example, the communication device 208 may sound a loud alarm in response to receiving an audible alarm signal. In another embodiment, the type of alert sent by the alert module 304 depends on how the activation signal was triggered. For example, pressing a single button may trigger a silent alarm while pressing two buttons simultaneously may trigger an audible alarm and a silent alarm. In another example, a user may say "Loud!" or "Silent!" or other phrase or word to trigger an audible and/or silent alarm, respectively, using voice activation.

In another embodiment, the alert module 304 may be programmable such that the user may customize how to trigger different alert types, such as a silent alarm, an audible alarm, and/or the like. For example, the user may specify that pressing two buttons sends a silent alarm every minute. Or, the user may specify that holding a button for five seconds triggers a loud alarm that sounds in five second intervals until disabled by the user. In another embodiment, the alert module 304 delays a predefined amount of time before sending an alert signal to the communication device 208. For example, the alert module 304 may start a thirty-second countdown before sending an alert signal to the communication device 208 and/or sounding an audible alarm. In one embodiment, this provides the user with an opportunity to disable the alert signal before being sent by the alert module 304. In another embodiment, the user programs the amount of time the alert module 304 delays before sending the alert signal.

In one embodiment, the alert module 304 configures one or more settings of the communication device 208. For example, the alert module 304 may send a signal to a smart phone to shut off the ring tone and/or place the phone in vibrate mode. In this manner, the smart phone may be silenced such that others are not aware that the alert module 304 sent an alert signal. Other settings may be configured by the alert module 304, such as locking the communication device 208, turning the communication device 208 off, or the like.

In various embodiments, the alert module 304 sends automated alerts regarding the status of the interchangeable personal security device 202. For example, the alert module 304 may send an alert to the communication device 208 in response to the battery level becoming low. In another example, the alert module 304 may send an alert if the interchangeable personal security device 202 is getting too far away from the communication device 208 or if the interchangeable personal security device 202 is having a difficult time maintaining a connection to the communication device 208.

In certain embodiments, the personal security apparatus 204 includes a notification module 306 configured to send a notification in response to the communication device 208 receiving the alert signal. In certain embodiments, the notification includes a message, medical information, a location, and/or the like. For example, a user having a heart attack may activate the interchangeable personal security device 202, which would send an alert signal to the communication device 208. The communication device 208, in response to receiving the alert signal, may send a predefined notification to one or more monitoring devices 212. The notification may include a message, such as "Help! I'm having a heart attack! Call 911!" The notification may also include the location and/or medical information of the person wearing the interchangeable personal security device 202.

In certain embodiments, the user customizes the notification sent by the notification module 306, including the message, medical information, or the like. In some embodiments, the user may also add one or more customized notifications that are sent in response to certain activation elements 106, 114 being triggered. For example, a particular notification may be sent in response to a specific voice command and a different notification may be sent in response to a button being pressed. Alternatively, a separate notification may be sent in response to the interchangeable personal security device 202 losing communication with the communication device 208, which may include the last known location of the interchangeable personal security device 202.

In one embodiment, the notification module 306 sends the notification to one or more predefined contacts. The one or more predefined contacts, in certain embodiments, are associated with one or more monitoring devices 212. In another embodiment, the notification module 306 sends a notification to one or more contacts that have been predefined by the user. For example, the user may select the contacts that may receive a notification from a list of contacts stored in the user's smart phone. The notification module 306, in another embodiment, is part of a computer program product running on the communication device 208, such as an application running on a smart phone. For example, a personal security application running on a smart phone may allow the user to configure various personal security settings, such as who to send a notification to, how to send the notification, what information the notification should include, or the like.

In one embodiment, the notification module 306 sends a notification to one or more contacts using short message service ("SMS"). For example, the one or more monitoring devices 212 may receive a text message from the communication device 208 that includes the notification information. In another embodiment, the notification module 306 sends an email to the one or more contacts. In a further embodiment, the notification module 306 sends an automated voice message to the one or more contacts. In some embodiments, the notification may be sent to the one or more contacts at specific time intervals. In one embodiment, the notification module 306 continuously sends a notification until at least one contact reacts to the notification, such as by calling emergency services, sending a reply message, calling the user, or the like.

In another embodiment, the notification module 306 posts a notification to one or more social networks associated with the user. For example, the notification module 306 may post a notification on the Twitter® page and/or a Facebook® page associated with the user. In some embodiments, the user selects the social network contacts to send the notification to. For example, the user may specify the Facebook® friends that should receive the notification, which may be posted on a webpage of a contact, such as a contact's wall, sent to the contact's Facebook® email address, sent as a private message, or the like.

Figure 4:
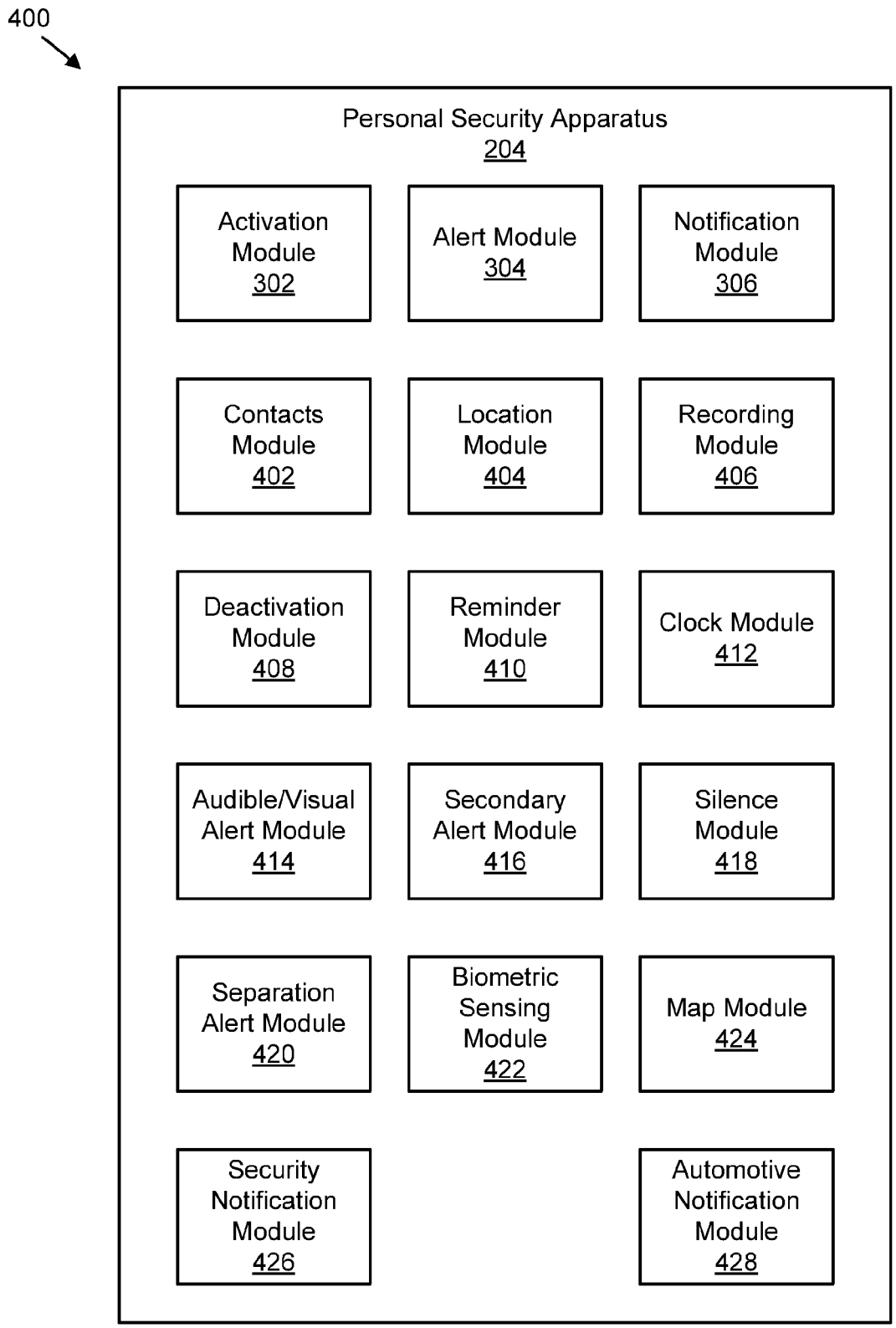
FIG. 4 is a schematic block diagram illustrating another embodiment of an interchangeable personal security apparatus.

FIG. 4 depicts another embodiment of an apparatus 400 that includes a personal security apparatus 204. In one embodiment, the personal security apparatus 204 includes an activation module 302, an alert module 304, and a notification module 306, which are substantially similar to the activation module 302, alert module 304, and notification module 306 of the apparatus 300 of FIG. 3. In a further embodiment, the personal security apparatus 204 includes a contacts module 402, a location module 404, a recording module 406, a deactivation module 408, a reminder module 410, a clock module 412, an audible/visual alert module 414, a secondary alert module 416, a silence module 418, a separation alert module 420, a biometric sensing module 422, a map module 424, a security notification module 426, and an automotive notification module 428, which are described in more detail below.

In one embodiment, the personal security apparatus 204 includes a contacts module 402 configured to store the one or more predefined contacts and to organize the one or more predefined contacts into one or more groups. In one embodiment, the one or more contacts may be stored on the communication device 208, such as a contact list in a smart phone or a friend list on a social network accessible by a network application.

In certain embodiments, the contacts module 402 groups contacts into one or more groups. In one embodiment, the contacts module 402 group contacts based on the user's location, the user's social circles, or the like. For example, a user may group contacts based on family relationships, work groups, travel groups, or the like, such that the user may notify contacts that will be able to provide the quickest assistance. Thus, a user may configure a personal security application on their smart phone to notify contacts in the "work" group between the hours of 8:00 AM and 5:00 PM in response to receiving an alert signal from the interchangeable personal security device 202 and may notify contacts in a different group during other hours. In one embodiment, a contact may be a member of more than one group.

As described above, multiple interchangeable personal security devices 202 may be in communication with a single communication device 208. In some embodiments, the contacts module 402 may assign a group of contacts to a specific interchangeable personal security device 202. For example, a child in a family of four may just have her parents in a contact group assigned to her interchangeable personal security device 202 whereas the father may have his spouse, one or more neighbors, extended family, or the like, in his contact group assigned to his interchangeable personal security device 202.

In certain embodiments, the contacts module 402 includes local emergency services, such as police and fire departments, as part of a contact group. In certain embodiments, the contacts module 402 automatically assigns local emergency services to every contact group, such that the emergency services are always notified. In another embodiment, the contacts module 402 gives the user the option to add the emergency services as a contact.

The personal security apparatus 204, in another embodiment, includes a location module 404 configured to send the location of the user in response to the communication device 208 receiving the alert signal. In one embodiment, the location module 404 adds the location of the user to the notification sent by the notification module 306. The location module 404, in some embodiments, uses a location service, such as a global positioning service ("GPS"), to determine the location of the user. For example, the communication device 208 may include a GPS function and the notification module 306 may include location information from the GPS in the communication device 208 in the notification sent by the notification module 306. In another embodiment, the alerting device 104 and/or the portable accessory 102 may include a location service and the location module 404 may include location information from the alerting device 104 and/or the portable accessory 102 in the alert signal sent to the communication device 208. In another embodiment, a monitoring device 212, in response to receiving a notification with the user's location, executes a map program, such as Google® Maps, to visually display the location of the user. The location of the user may be a location of the alerting device 104 and/or portable accessory 102 or may be a location of the communication device 208, or both.

In certain embodiments, the location module 404 provides the location of the user as an address. In some embodiments, the location module 404 provides the location of the user as degrees of latitude and longitude. The location module 404, in other embodiments, determines the directions from the monitoring device 212 to the user and displays the directions on the monitoring device 212. In one embodiment, the location module 404 continuously transmits the user's location in response to the user activating a location transmission mode using one or more activation elements 106, 114. In certain embodiments, the location module 404 transmits the location of the interchangeable personal security device 202 in response to the interchangeable personal security device 202 losing communication with the communication device 208. In one embodiment, the communication device 208 includes a location service and transmits a location of the communication device 208 in response to losing communication with the personal security device 202. In another embodiment, the personal security device 202 includes a location service and sends a location of the personal security device 202 with the alert signal.

In some embodiments, the location of the interchangeable personal security device 202 may be tracked using a website, a mapping program, or the like. For example, if a user wearing the interchangeable personal security device 202 is missing, another person may use information on a website or other location to determine a location of the interchangeable personal security device 202. The person may start tracking the interchangeable personal security device 202 with or without a notification. In one embodiment, the location module 404 transmits a location of the interchangeable personal security device 202 or transmits a location in response to an inquiry. In one embodiment, the location module 404 continuously sends the location of the interchangeable personal security device 202 by SMS, email, to a website corresponding to the interchangeable personal security device 202 or the user, or the like.

In certain embodiments, the personal security apparatus 204 includes a recording module 406 configured to record content in response to a user interacting with one or more activation elements 106, 114. In one embodiment, the recording module 406 records audible sounds using a sound capture device, such as a microphone. In another embodiment, the recording module 406 captures still images and/or video using an image capture device, such as a digital camera. In certain embodiments, recording module 406 stores the content on the interchangeable personal security device 202 and transfers content to external devices using a wireless or wired connection, such as WiFi, USB, or the like. In some embodiments, the recording module 406 sends the content to one or more monitoring devices 212 as part of a notification. In one embodiment, the recording module 406 records content for a predetermined amount of time. The recording module 406, in certain embodiments, records content until the user interacts with one or more activation elements 106, 114. For example, a user may interact with one or more activation elements 106, 114 to stop recording.

In one embodiment, the personal security apparatus 204 includes a deactivation module 408 that cancels sending a notification to one or more contacts in response to receiving a deactivation signal. In one embodiment, the communication device 208 does not send a notification in response to receiving the deactivation signal. In certain embodiments, the deactivation module 408 sends a deactivation signal in response to the user deactivating the alert signal within a predetermined amount of time. In another embodiment, the deactivation module 408 sends a deactivation signal in response to the user interacting with one or more activation elements 106, 114. For example, a user may press two buttons in a predetermined order or a predetermined number of times in order to send a deactivation signal.

In one embodiment, the deactivation module 408 receives a deactivation password entered by a user in order to send a deactivation signal. For example, a user may enter a password on a smart phone executing a personal security application. If the password is a valid deactivation password, the communication device 208 may not send a notification to one or more contacts. In certain embodiments, the deactivation module 408 receives a fake or "spoof" password designed to give the impression that the communication device 208 has been deactivated when it is still active. For example, a user may be under duress to deactivate sending the alert signal and/or the notification. The user may enter a predetermined fake password to make it appear that the communication device 208 has been deactivated. The communication device 208, however, may continue to send the notification until a valid deactivation password has been provided.

The personal security apparatus 204, in another embodiment, includes a reminder module 410 configured to periodically generate an audible sound. The reminder module 410 may generate an audible sound in response to a predetermined amount of time elapsing. In another embodiment, the reminder module 410 generates an audible sound based on a predetermined schedule. For example, a user may set a reminder to take his pills every day at 8:00 AM. The reminder module 410 may be programmed to generate a sound every day at that time. The reminder module 410, in some embodiments, consistently generates the audible sound until the user interacts with one or more of the activation elements 106, 114.

In certain embodiments, the personal security apparatus 204 includes a clock module 412 configured to indicate and keep time. The interchangeable personal security device 202, for example, may include a digital clock disposed on a hidden portion of the personal security device 202. In some embodiments, the reminder module 410 uses the clock module 412 to set alarms, timers, or the like, that generate an audible sound in response to a predetermined amount of time elapsing.

In one embodiment, the personal security apparatus 204 includes an audible/visual alert module 414 that transmits an audible alert and/or a visual alert in response to activating an activation element 106, 114 of the one or more activation elements 106, 114. For example, as described above, the interchangeable personal security device 202 may sound a loud alarm when the user actuates one or more activation elements 106, 114. In another example, the interchangeable personal security device 202 may include visual elements, such as one or more lights that turn on, flicker, or the like, in response to the user actuating one or more activation elements 106, 114. In some embodiments, the audible/visual alert module 414 transmits a combination of audible and visual alert signals. For example, after a user actuates one or more activation elements 106, 114, the audible/visual alert module 414 may sound a loud alarm and flicker one or more lights on and off. In this manner, the audible/visual alert module 414 may warn and/or alert others within the proximity of the interchangeable personal security device 202.

In one embodiment, the power supply for the communication device 208 may provide power for the audible/visual alert module 414. For example, in one embodiment the communication device 208 may include a more powerful power supply than the personal security device 202, and the communication device 208 may provide power for the audible/visual alert module 414, to provide a brighter, louder, or otherwise more powerful audible and/or visual alert.

In a certain embodiment, the communication device 208 and the audible/visual alert module 414 may respond to different activation signals. For example, in one embodiment, a user may activate one or more activation elements in one way to trigger a first activation signal that triggers an alerting element to send an alert signal to the communication device 208. In a further embodiment, the user may activate the activation elements in a different way (e.g., by pressing a different button, pressing a different sequence of buttons, or the like), to trigger a second activation signal, that triggers the audible/visual alert module 414 to transmit an audible and/or visual alert. In certain embodiments, the first activation signal may be different from the second activation signal, so that the audible/visual alert module 414 can be activated separately from the communication device 208.

The personal security apparatus 204, in another embodiment, includes a secondary alert module 416 that sends a notification to one or more predefined contacts in response to receiving an activation signal from the one or more activation elements 106, 114 and not being in communication with a communication device 208 configured to send a notification to the one or more predefined contacts. For example, if the interchangeable personal security device 202 is not in communication with the communication device 208, the secondary alert module 416 sends a notification to one or more predefined contacts. In one embodiment, the secondary alert module 416 is programmed with one or more predefined contacts and a notification message that is sent to the one or more predefined contacts. In another embodiment, the secondary alert module 416 uses a network 206, 210, which may include a cell phone network, to send a notification to one or more predefined contacts.

In certain embodiments, the personal security apparatus 204 includes a silence module 418 that sends a silence signal to the communication device 208 in response to the alert signal. In some embodiments, the communication device 208 enters a muted state in response to the silence signal. For example, a smart phone may disable its ring tone and vibrate mode, may go into vibrate mode, shut down, or the like, in response to receiving a silence signal from the silence module 418. In some embodiments, the communication device 208 further enters a state where an electronic display of the communication device 208 is deactivated in response to the silence signal. For example, the silence module 418 may send a silence signal to the communication device 208 and the communication device may disable all audio and visual functions so that the communication device 208 may not alert an attacker of the presence of the communication device 208 while the communication device 208 continues to receive alert notifications from the personal security device 202, send notifications to monitoring devices 212, etc. In another embodiment, the silence module 418 sends a silence signal to the communication device 208 along with an alert signal. In another embodiment, the communication device 208 may be pre-programmed with a default setting to enter a silent mode when receiving a communication from the personal security device 202. In this manner, others within the proximity of the communication device 208 may not be made aware that the interchangeable personal security device 202 is in communication with the communication device 208 and that the communication device 208 is sending notifications to one or more monitoring devices 212.

In one embodiment, the personal security apparatus 204 includes a separation alert module 420 that sends a separation alert in response to the alerting device 104 losing communication with the communication device 208 after the communication device 208 receives the alert signal. For example, the interchangeable personal security device 202 may be in wireless communication with a smart phone using a Bluetooth® connection. While in an alert mode after receiving an alert signal, if the smart phone loses the connection with the interchangeable personal security device 202, e.g., by going outside the range of the Bluetooth® connection, the separation alert module 420 may send an activation signal. The alert mode, in one example, is a time after receiving an alert signal and before some type of a cessation of the alert mode, such as by a deactivation signal, expiration of a time limit, etc. In another embodiment, the separation alert module 420 may not send a separation alert when not in an alert mode, for example if no alert signal has been received.

In another embodiment, the separation alert module 420 sends an activation signal in response to the interchangeable personal security device 202 not moving for a predefined amount of time. For example, a motion sensor device may be programmed to send an activation signal in response to not sensing motion for thirty minutes, ten hours, or the like. In another example, if an alert signal was previously sent and before a deactivation event, such as a deactivation signal, the separation alert module 420 may sense no movement of the personal security device 202 for a predetermined time and may send an activation signal. In another example, the separation alert module 420 sends a notification after sensing that the communication device 208 has not moved for a specified period of time while in an alert mode. In another embodiment, the separation alert module 420 sends an activation signal in response to one or more components of the interchangeable personal security device 202 malfunctioning.

In one embodiment, the personal security device 202 includes a communication capability that allows the personal security device 202 to send an alert signal to a device other than the communication device 208. For example, the personal security device 202 may include a cellular telephone, radio, WiFi, etc. capability that is activated in response to losing communication with the communication device 208. The alert may include a location of the personal security device 202 that is determined by a location service associated with the personal security device 202. For example, the location service may be determined by the cellular telephone service, such as by triangulation, by determining a location of one or more cellular towers in communication with the personal security device 202, etc. In another embodiment, the personal security device 202 includes a GPS capability and the alert signal sent by the personal security device 202 may include location information from the GPS service.

In one embodiment, the location service and/or additional communication capability of the personal security device 202 is located in the alerting device 104. In another embodiment, the location service and/or additional communication capability of the personal security device 202 is located in the portable accessory 102. For example, the portable accessory 102 may have a cellular telephone, radio, or other communication capability that is capable of communication at a distance more than a few feet and the communication capability may be disabled before an alert signal or after an alert signal and while the communication device 208 is in communication with the personal security device 202, and the communication capability may be enabled, for example by the separation alert module 420, after an alert signal and after the personal security device 202 loses communication with the communication device 208. In other embodiments, the additional communication capability of the personal security device 202 may be activated in other situations, for example, by user input through an activation element 106, 114, by pressing a certain combination of activation elements 106, 114, by a voice command, etc.

For example, an alerting device 104 of a personal security device 202 may be designed for communication with the communication device 208 when the communication device 208 is within a short distance of the personal security device 202 while the portable accessory 102 of the personal security device 202 may include a communication capability for longer range communications. In one embodiment, the portable accessory 102 may include a power supply sufficient for the longer range communications. The power supply may be rechargeable, in one embodiment, or may include a disposable battery to be replaced. In another embodiment, the power supply for the longer range communications may be deactivated under typical use of the personal security device 202 and may be activated under certain circumstances, such as after an alert signal and then after loss of communication with the communication device 208. In another embodiment, the personal security device 202 may transmit occasional signals using the longer range communications to save power and may hibernate the longer range communications capability between transmissions.

In one embodiment where the portable accessory 102 includes communication functionality separate from the alerting device 104, the separation alert module 420 places the portable accessory 102 into a communication mode in response to losing communication with the communication device 208. The communication mode may include activating a cellular communication mode, Bluetooth®, Wi-Fi, or the like. As discussed above, in some embodiments, the separation alert module 420 places the portable accessory 102 into a communication mode in response to losing communication with the communication device 208 after the communication device 208 receives an alert signal. For example, after an alert signal has been sent (indicating that the alerting device 104 and/or the portable accessory 102 has been activated), the separation alert module 420 may enable a cellular communication capability of the portable device 102 such that the portable device 102 may continue to communicate with a cellular network even though communication with the communication device 208 is lost. Alternatively, the separation alert module 420 enables other functionality of the portable accessory 102, such as an alarm, location services, or the like, in response to losing communication with the communication device 208.

The personal security apparatus 204, in one embodiment, includes a biometric sensing module 422 that senses biometric information associated with a user and sends an activation signal in response to the interchangeable personal security device 202 failing to sense biometric information associated with the user. For example, the interchangeable personal security device 202 may include a biometric monitor device that sends an activation signal in response to failing to sense biometric information, such as a user's pulse. In other embodiments, the biometric sensing module 422 may send an activation signal in response to sensing enhanced biometric information, such as an increased heart rate, increased breathing rate, or the like, which may signal certain emotions such as fear, anger, or the like.

In another embodiment, the biometric sensing module 422 may send an activation signal in response to not sensing biometric information. In one example, the biometric sensing module 422 may send an activation signal in response to not sensing biometric information after the activation module 302 receives an activation signal from one or more activation elements 106, 114. For instance, after receiving an activation signal from one or more activation elements 106, 114, the biometric sensing module 422 may sense biometric data from a user and the biometric data may cease, possibly indicating a separation of the personal security device 202 from the user or that the user is deceased. In another embodiment, the biometric sensing module 422 may sense biometric data from a user independent of the activation module 302 receiving an activation signal.

The personal security apparatus 204, in one embodiment, includes a map module 424 that displays a recommended safe route between origin and destination points. In the depicted embodiment, the map module 424 is part of the personal security apparatus 204. However, in another embodiment, the map module 424 may be part of a communication device 208, or another device. For example, in one embodiment, the map module 424 may be an application on a cell phone, tablet, or other portable electronic device. In another embodiment, the map module 424 may be a web application.

In another embodiment, the map module 424 may communicate with a safe route system (not shown) that monitors conditions with regard to safety. For example, the system may store street light locations, crime data, business hours for stores, gas stations, etc., amount of traffic on a roadway, and other information that may assist in identifying a route that may be thought to be safer than other routes that may be in areas of high crime, dimly lit, etc.

In various embodiments, origin and/or destination points for the recommended safe route may be entered by a user, selected by the user from a list of predetermined locations (such as work, home, and the like), automatically determined based on a user's location, selected from a list of location search results, or the like. In certain embodiments, the map module 424 may determine the recommended safe route by identifying multiple routes between the origin and destination points, and evaluating a safety factor for each of the possible routes. In various embodiments, a safety factor for a route may be based on lighting along the route, open businesses along the route, reported crime along the route, or the like, or a combination of individual factors. In a further embodiment, the map module 424 may select the recommended safe route from the multiple possible routes based on the evaluated safety factors.

In one embodiment, determining a safety factor for a route may include whether stores, gas stations, and the like are open or the like. For example, the safe route system may gather information regarding store and business hours and may identify a safer route based on how many stores and businesses are open along the route. In another embodiment, the safe route system integrates with a system that provides a shortest route to a location to identify a route that has safety factors as well as shortest route considerations. A user, in one example, may identify certain traits of a route with regard to safety and the map module 424 may work with information from a safe route system and a shortest route system to identify a route that is shortest while considering safety factors, a minimum level of safety in certain areas, etc.

The personal security apparatus 204, in one embodiment, includes a security notification module 426 that sends a notification to a security force in response to the communication device 208 receiving the alert signal. In the depicted embodiment, the security notification module 426 is part of the personal security apparatus 204. However, in another embodiment, the security notification module 426 may be part of a communication device 208, or another device. For example, in one embodiment, the security notification module 426 may be an application on a cell phone, tablet, or other portable electronic device.

In a certain embodiment, a security force, such as a campus security department, may provide an opt-in program allowing a user to register with the security force so that a notification from a security notification module 426, for a registered user, may indicate that an emergency has occurred or is occurring. In one embodiment, the security notification module 426 may send a notification to the security force that includes a location of the user. For example, in a further embodiment, the security notification module 426 may send a text message with the user's GPS coordinates to the security force. In another embodiment, the security notification module 426 may send a notification to the security force that allows the security force to connect to an active GPS location signal for the user.

The personal security apparatus 204, in one embodiment, includes an automotive notification module 428 that sends a notification via an automobile communication service, in response to the alert signal. In certain embodiments, an automobile communication service, such as the OnStar® service provided by General Motors, may connect a driver or passenger to representatives for emergency services. In a further embodiment, an automotive notification module 428 may link the personal security apparatus 204 to a car's OnStar® service, or a similar automobile communication service, and may send a notification via the automobile communication service in response to an alert signal.

The automotive notification module 428, in one embodiment, may be a communication device 208 and may have similar functionality as the communication device 208 described above. For example, the automotive notification module 428 may have similar capabilities to a cellular phone or other device that receives a signal from the personal security device 202 and sends a notification to a monitoring device 212. In one embodiment, the automotive notification module 428 may act in parallel with another communication device 208 to send an alert or may send an alert when another primary communication device 208 is not functioning. For example, if an attacker throws a cell phone out of a vehicle that was in communication with the personal security device 202, the automotive notification module 428 may send an alert in response to receiving an alert from the personal security device 202. The automotive notification module 428 may provide additional security to a user when another communication device 208 is not functioning or is not present.

Figure 5:
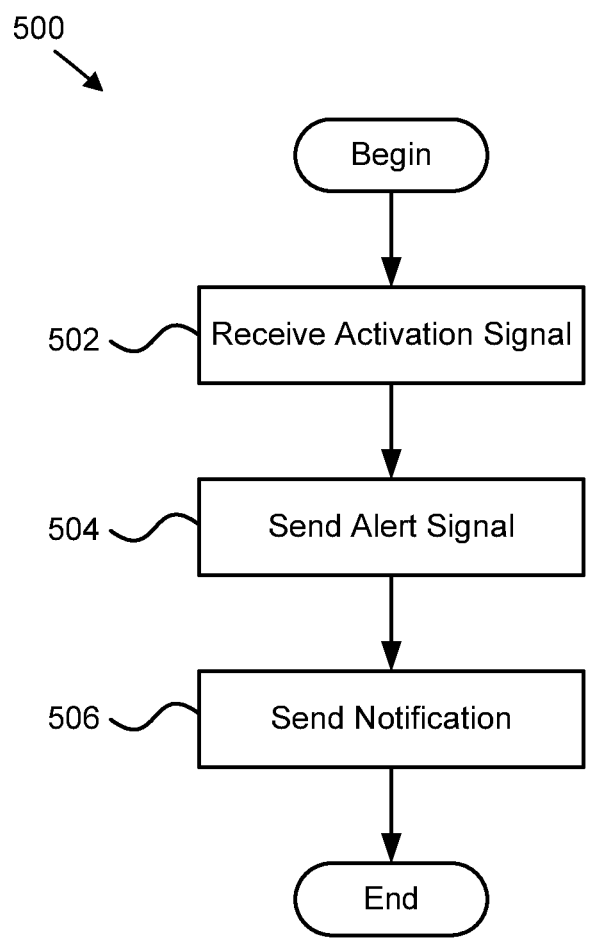
FIG. 5 is a schematic flow chart diagram illustrating one embodiment of a method for personal security.

FIG. 5 depicts one embodiment of a method 500 for personal security. In one embodiment, an activation module 302 receives 502 an activation signal in response to a user interacting with one or more activation elements 106, 114. In another embodiment, an alert module 304, which is in wireless communication with a communication device 208, wirelessly sends 504 an alert signal to the communication device 208 in response to receiving the activation signal. A notification module 306, in a further embodiment, sends 506 a notification to one or more predefined contacts in response to the communication device 208 receiving the alert signal, and the method 500 ends.

Figure 6:
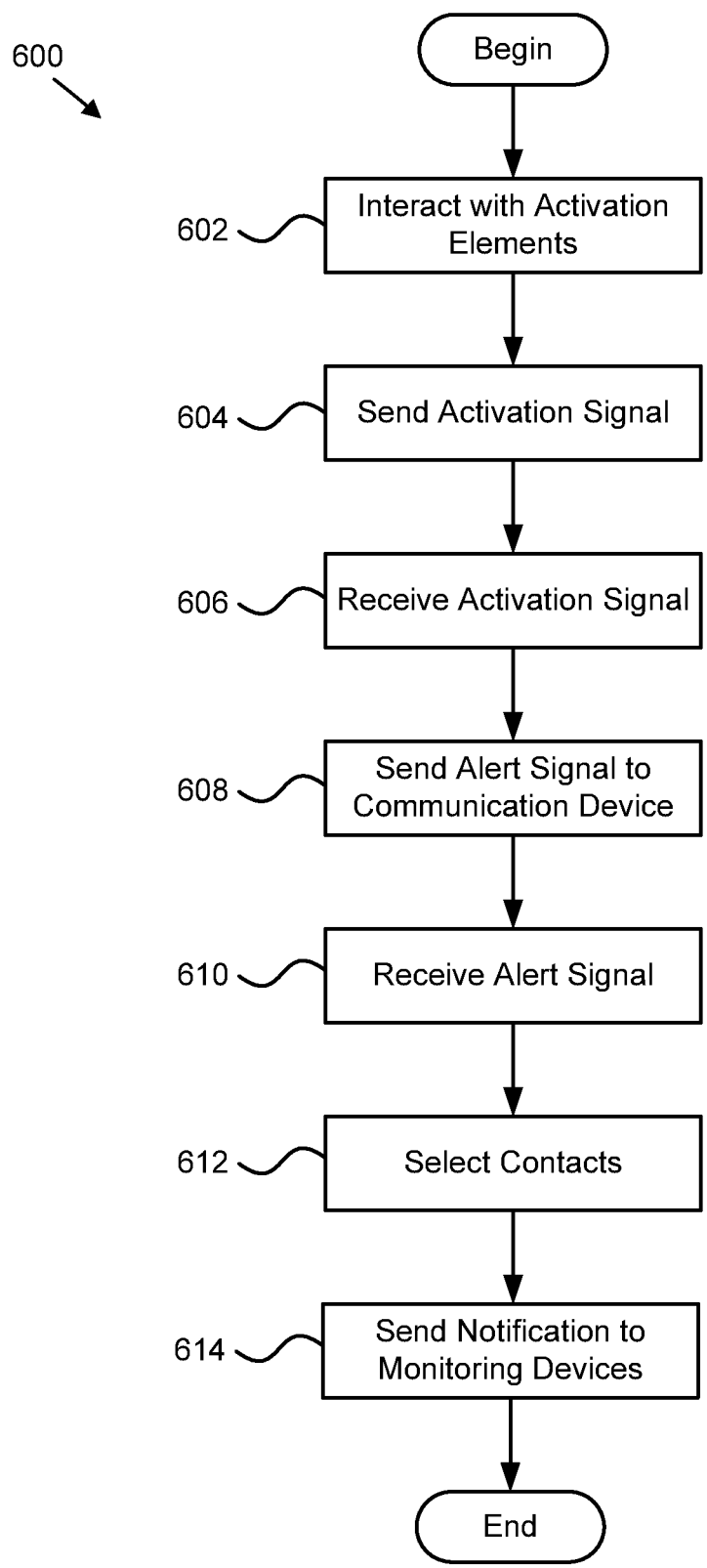
FIG. 6 is a schematic flow chart diagram illustrating another embodiment of a method for personal security.

FIG. 6 depicts another embodiment of a method 600 for personal security. In one embodiment, a user interacts 602 with one or more activation elements 106, 114 located on the interchangeable personal security device 202. In one embodiment, an activation signal is sent 604 in response to the user interacting with one or more activation elements 106, 114. In another embodiment, the type of activation signal that is sent 604 depends on the manner in which the user interacted with the one or more activation elements 106, 114. For example, a user may press two buttons quickly, hold one button down, speak into the personal security device 202, or the like, to activate the personal security device 202 and trigger different actions.

In certain embodiments, an activation module 302 receives 606 an activation signal in response to the user interacting with one or more activation elements 106, 114. Depending on the type of activation signal that was sent, in one embodiment, an alert module 304 sends 608 an alert signal to the communication device 208 in response to receiving the activation signal. In some embodiments, the alert module 304 sends a silent alarm such that others cannot tell the alert module 304 is communicating with the communication device 208. In other embodiments, the alert module 304 sends an audible alarm designed to warn and/or alert others around the interchangeable personal security device 202.

In one embodiment, a communication device 208 receives 610 the alert signal and selects 612 one or more contacts to send 614 a notification to. In one embodiment, a notification module 306 sends 614 a notification to one or more monitoring devices 212 associated with one or more predefined contacts, and the method 600 ends. In certain embodiments, a contacts module 402 organizes contacts into one or more groups and assigns contacts to one or more interchangeable personal security devices 202. In some embodiments, the notification sent by the notification module 306 includes a message, a user's location, the user's medical information, or the like.

Embodiments of the present invention may be practiced in other specific forms. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes," "has," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. An apparatus comprising:
   an alerting device comprising an alerting element, the alerting device being interchangeable with a plurality of portable accessories, wherein the alerting device comprises a wireless communication capability consisting of a short-range wireless communication capability;
   a communication device that comprises a wireless communication capability consisting of a long-range wireless communication capability;
   a portable accessory formed to receive the alerting device, the alerting device inserted within a compartment of the portable accessory, the portable accessory comprising the communication device, the communication device communicatively coupled to the alerting device using one or more of a short-range wireless communication connection and a wired connection in response to the alerting device being inserted into the portable accessory; and
   one or more activation elements disposed on the portable accessory and formed to activate the alerting device wherein the alerting element sends an alert signal to the communication device in response to receiving an activation signal from the one or more activation elements, and wherein the communication device of the portable accessory transmits a notification directly to one or more contacts using the long-range wireless communication capability in response to receiving the alert signal, the one or more contacts programmed by a user and stored on the communication device.

2. The apparatus of claim 1, wherein the communication device comprises one or more of a satellite communication device, a short wave radio communication device, a two-way radio communication device, and a cellular network communication device.

3. The apparatus of claim 1, wherein the alerting device is in communication with the communication device and sends the alert signal to the communication device in response to receiving the activation signal.

4. The apparatus of claim 3, wherein the communication device notifies one or more predefined contacts that an alert signal was sent in response to receiving the alert signal.

5. The apparatus of claim 1, wherein the communication device comprises a power supply separate from a power supply for the alerting device, the power supply for the communication device providing more power than the power supply for the alerting device.

6. The apparatus of claim 5, wherein the power supply for the communication device comprises a battery, the battery comprising one or more of a rechargeable battery and a disposable battery.

7. The apparatus of claim 5, wherein the power supply for the communication device comprises a fuel cell, the fuel cell capable of maintaining an isolated fuel supply until the fuel cell is activated.

8. The apparatus of claim 1, wherein the communication device is powered on in response to the activation signal.

9. The apparatus of claim 1, further comprising an audible/visual alert module that transmits one or more of an audible alert and a visual alert in response to activating an activation element of the one or more activation elements, wherein a power supply for the communication device provides power for the audible/visual alert module.

10. The apparatus of claim 9, wherein alerting element sends the alert signal to the communication device in response to a first activation signal from the one or more activation elements and the audible/visual alert module transmits one or more of the audible alert and the visual alert in response to a second activation signal from the one or more activation elements, the first activation signal differing from the second activation signal.

11. A system comprising:
   a communication device that comprises a wireless communication capability consisting of a long-range wireless communication capability;
   an interchangeable alerting device shaped to fit within two or more portable accessories, wherein at least one of the portable accessories comprises the communication device, and wherein the interchangeable alerting device comprises a wireless communication capability consisting of a short-range wireless communication capability;

an activation module in the alerting device that receives an activation signal in response to a user interacting with one or more activation elements of the alerting device;

an alert module in communication with the communication device that sends an alert signal to the communication device in response to receiving the activation signal, the communication device communicatively coupled to the alerting device using one or more of a short-range wireless communication connection and a wired connection in response to the alerting device being inserted within the compartment of the portable accessory; and a notification module that sends a notification in response to the communication device receiving the alert signal, the communication device sending the notification directly to one or more predefined contacts using the long-range wireless communication capability, the one or more predefined contacts programmed by a user and stored on the communication device.

12. The system of claim 11, wherein the communication device sends the notification to one or more predefined contacts by communicating with a single distribution device that distributes the notification to the one or more predefined contacts.

13. The system of claim 11, further comprising a second communication device separate from the portable accessories, the second communication device receiving the alert signal and sending a notification to one or more additional predefined contacts.

14. The system of claim 11, further comprising a map module that displays a recommended safe route between origin and destination points, wherein the map module determines the recommended safe route based on one or more of lighting, open businesses, and reported crime.

15. The system of claim 11, further comprising a security notification module that sends a notification to a security force in response to the communication device receiving the alert signal, the notification to the security force comprising a location of the user.

16. The system of claim 11, further comprising an automotive notification module that sends a notification via an automobile communication service, in response to the alert signal.

17. The system of claim 11, further comprising a contacts module that stores the one or more predefined contacts and organizes the one or more predefined contacts into one or more groups.

18. The system of claim 11, further comprising a location module that sends a location of the user in response to the communication device receiving the alert signal.

19. A method comprising:

receiving, in an alerting device, an activation signal in response to a user interacting with one or more activation elements of the alerting device, the alerting device interchangeable and shaped to fit within two or more portable accessories, wherein the alerting device comprises a wireless communication capability consisting of a short-range wireless communication capability, and wherein at least one of the portable accessories comprises a communication device, the communication device communicatively coupled to the alerting device using one or more of a short-range wireless communication connection and a wired connection in response to the alerting device being inserted within the compartment of the portable accessory;

sending an alert signal to the communication device using one or more of the short-range wireless communication connection and the wired connection in response to receiving the activation signal; and sending a notification in response to the communication device receiving the alert signal, the communication device sending the notification directly to one or more predefined contacts using a long-range wireless communication capability of the communication device, the one or more predefined contacts programmed by a user and stored on the communication device.

* * * * *